United States Patent
Tarshish-Shapir et al.

(10) Patent No.: US 10,242,290 B2
(45) Date of Patent: Mar. 26, 2019

(54) METHOD, SYSTEM, AND USER INTERFACE FOR METROLOGY TARGET CHARACTERIZATION

(71) Applicant: KLA-Tencor Corporation, Milpitas, CA (US)

(72) Inventors: Inna Tarshish-Shapir, Haifa (IL); Yoel Feler, Haifa (IL); Anat Marchelli, Kiryat Yam (IL); Berta Dinu, Migdal Haemek (IL); Vladimir Levinski, Migdal HaEmek (IL); Boris Efraty, Carmiel (IL); Nuriel Amir, St. Yokneam (IL); Mark Ghinovker, Yoqneam Ilit (IL); Amnon Manassen, Haifa (IL); Sigalit Robinzon, Timrat (IL)

(73) Assignee: KLA-Tencor Corporation, Milpitas, CA (US)

(*) Notice: Subject to any disclaimer, the term of this patent is extended or adjusted under 35 U.S.C. 154(b) by 581 days.

(21) Appl. No.: 14/152,562

(22) Filed: Jan. 10, 2014

(65) Prior Publication Data

US 2014/0136137 A1 May 15, 2014

Related U.S. Application Data

(63) Continuation of application No. PCT/US2013/069263, filed on Nov. 8, 2013.
(Continued)

(51) Int. Cl.
*G01R 31/28* (2006.01)
*G06K 9/52* (2006.01)
(Continued)

(52) U.S. Cl.
CPC ......... *G06K 9/522* (2013.01); *G01N 21/4788* (2013.01); *G06T 7/0004* (2013.01);
(Continued)

(58) Field of Classification Search
CPC ................. G06K 9/522; G06T 7/0004; G06T 2207/30148; H01L 22/30; H01L 22/12; G01N 21/4788; G01B 2210/56
(Continued)

(56) References Cited

U.S. PATENT DOCUMENTS 6,336,086 B1  1/2002  Perez et al.
7,111,256 B2  9/2006  Seligson et al.
(Continued)

FOREIGN PATENT DOCUMENTS

TW  200406586 A  5/2004
TW  201120466 A  6/2011
(Continued)

OTHER PUBLICATIONS

Raymond, C.J. 2011, "Improved overlay control using robust outlier removal methods", Proc. SPIE 7971, Metrology, Inspection, and Process Control for Microlithography XXV, 79711G, disclosing regression based outlier removal methods.
(Continued)

*Primary Examiner* — John H Le
(74) *Attorney, Agent, or Firm* — Suiter Swantz pc llo

(57) ABSTRACT

Methods and systems are provided, which identify specified metrology target abnormalities using selected metrics and classify the identified target abnormalities geometrically to link them to corresponding sources of error. Identification may be carried out by deriving target signals such as kernels from specified regions of interest (ROIs) from correspond-
(Continued)

ing targets on a wafer, calculating the metrics from the target signals using respective functions and analyzing the metrics to characterize the targets.

24 Claims, 16 Drawing Sheets

Related U.S. Application Data

(60) Provisional application No. 61/724,846, filed on Nov. 9, 2012.

(51) Int. Cl.
 *G06T 7/00* (2017.01)
 *H01L 21/66* (2006.01)
 *G01N 21/47* (2006.01)

(52) U.S. Cl.
 CPC ......... *H01L 22/12* (2013.01); *G01B 2210/56* (2013.01); *G06T 2207/30148* (2013.01); *H01L 22/30* (2013.01)

(58) Field of Classification Search
 USPC ........... 702/81, 108, 35; 430/5, 30; 356/401, 356/636
 See application file for complete search history.

(56) References Cited

U.S. PATENT DOCUMENTS

| | | | | |
|---|---|---|---|---|
| 7,242,477 B2* | 7/2007 | Mieher | ................ | G01N 21/956 356/401 |
| 7,310,789 B2 | 12/2007 | Seligson et al. | | |
| 7,415,386 B2 | 8/2008 | Burch et al. | | |
| 7,695,876 B2* | 4/2010 | Ye | ................ | G03F 1/14 382/145 |
| 8,035,824 B2* | 10/2011 | Ausschnitt | ......... | B81C 99/0065 356/401 |
| 8,057,967 B2* | 11/2011 | Ye | ................ | G03F 1/14 257/48 |
| 8,318,391 B2* | 11/2012 | Ye | ................ | G03F 1/14 257/48 |
| 8,525,993 B2 | 9/2013 | Rabello et al. | | |
| 2003/0223630 A1* | 12/2003 | Adel | ................ | G03F 7/705 382/145 |
| 2004/0040003 A1* | 2/2004 | Seligson | ................ | G03F 7/705 382/151 |
| 2004/0233441 A1* | 11/2004 | Mieher | ................ | G01N 21/956 356/401 |
| 2007/0050749 A1* | 3/2007 | Ye | ................ | G03F 1/14 430/30 |
| 2007/0186206 A1 | 8/2007 | Abrams et al. | | |
| 2009/0192765 A1 | 7/2009 | Gattiker | | |
| 2010/0151364 A1* | 6/2010 | Ye | ................ | G03F 1/14 430/5 |
| 2010/0211903 A1 | 8/2010 | Luque | | |
| 2012/0021343 A1* | 1/2012 | Ye | ................ | G03F 1/14 430/5 |
| 2013/0035888 A1* | 2/2013 | Kandel | ................ | G03F 7/70633 702/81 |

FOREIGN PATENT DOCUMENTS

| | | | | |
|---|---|---|---|---|
| WO | WO 2012138758 A1 * | 10/2012 | ......... | G03F 7/70633 |
| WO | 2013092106 A1 | 6/2013 | | |

OTHER PUBLICATIONS

U.S. Appl. No. 13/834,915, filed Mar. 13, 2013 (not yet published).
Office Action dated Apr. 6, 2017 for Taiwan Patent Application No. 102140800.
Seligson, Joel et al., "Target Noise in overlay metrology", Proceedings vol. 5375, Metrology, Inspection, and Process Control for Microlithography XVIII, https://www.spiedigitallibrary.org/conference-proceedings-of-spie/5375/0000/Target-noise-in-overlay-metrology/10.1117/12.534515.short?SSO=1, 10 pages.

* cited by examiner

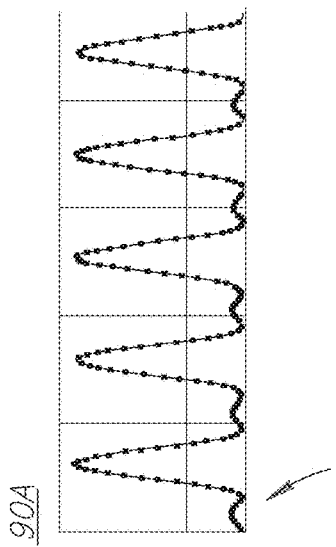
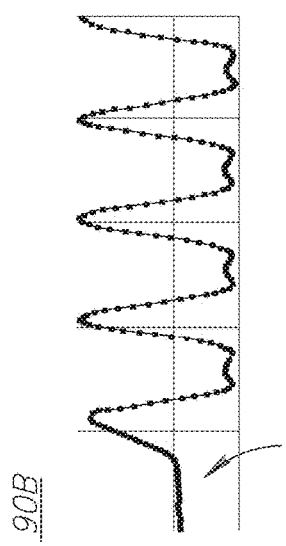
Figure 2C
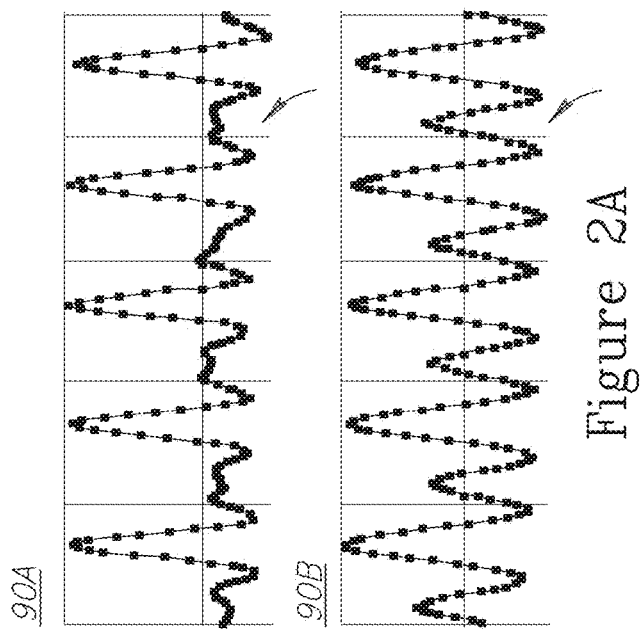
Figure 2A
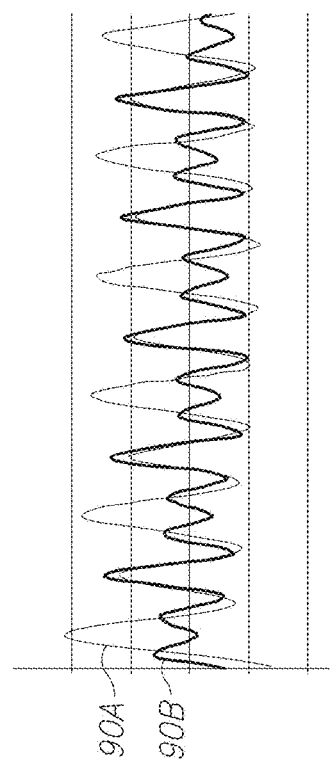
Figure 2B

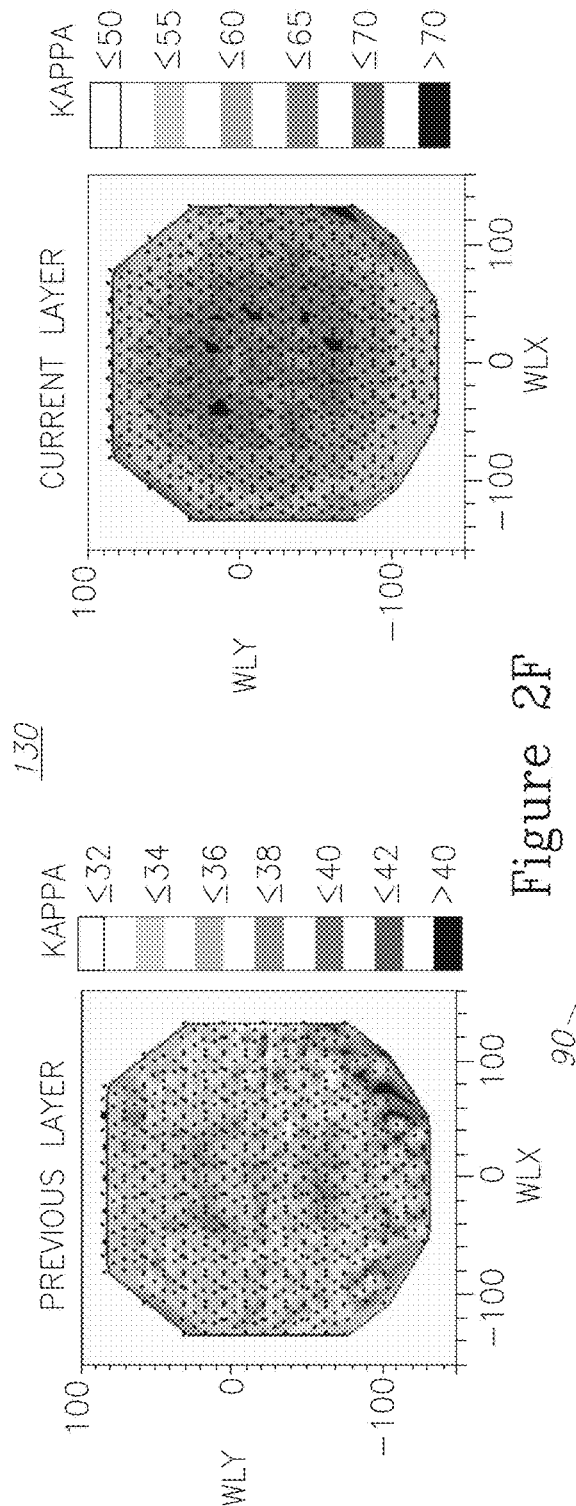
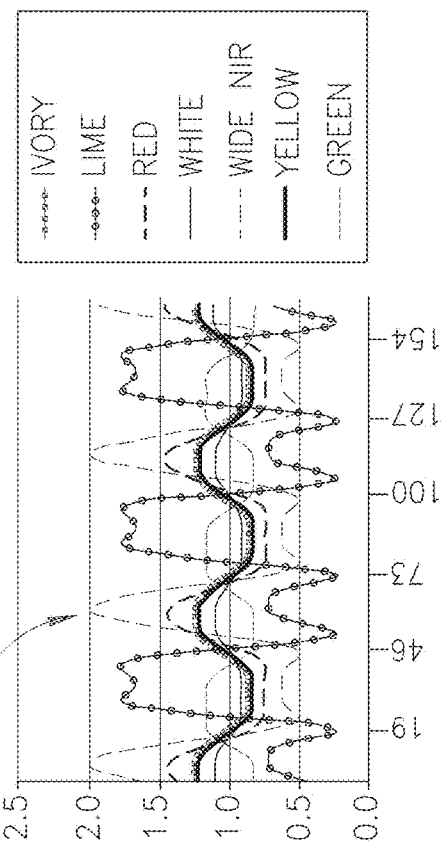
Figure 2F
Figure 2G

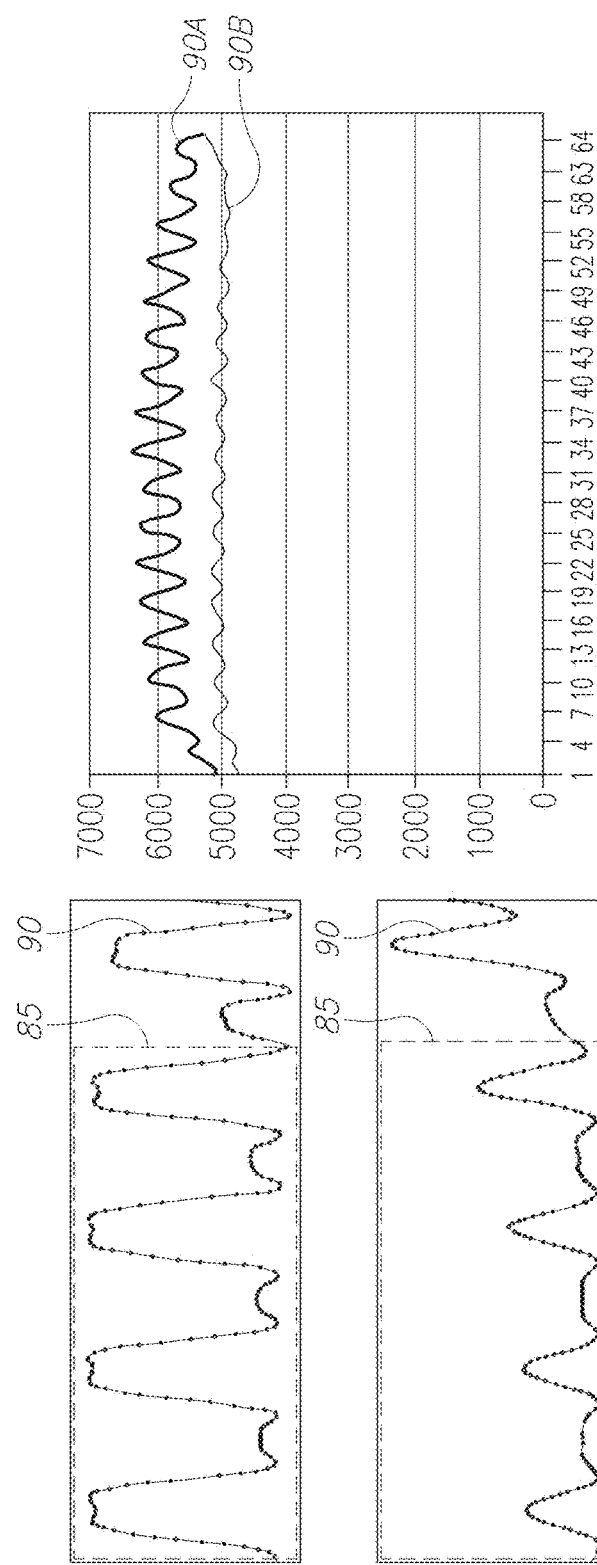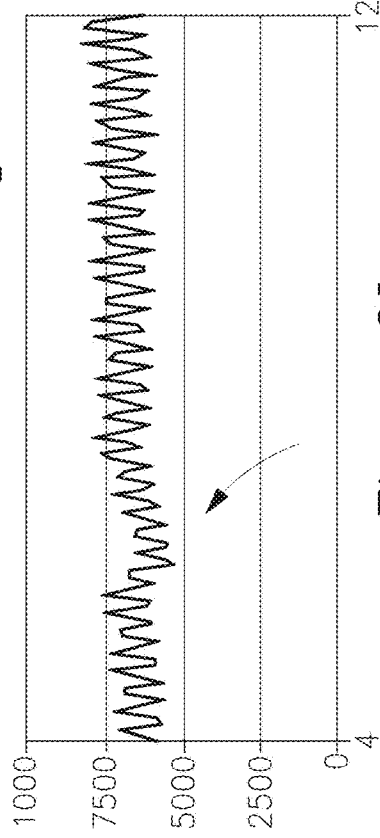

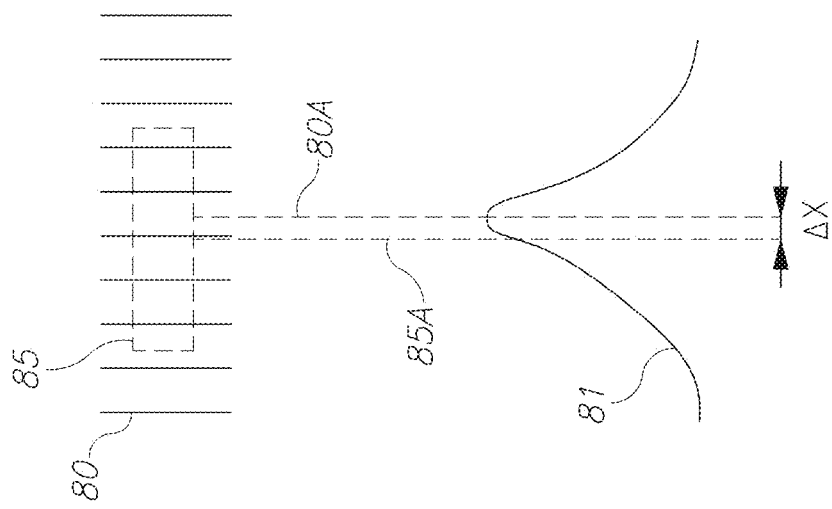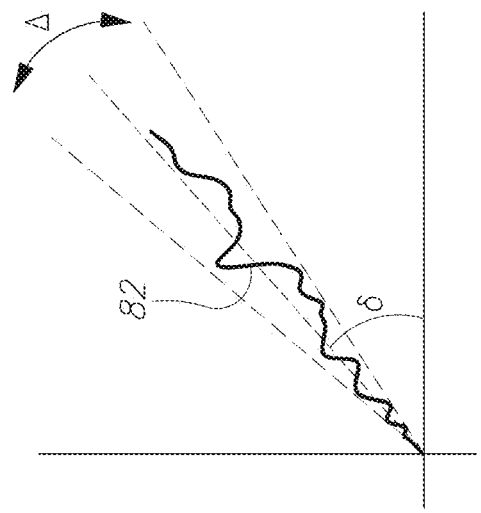
Figure 3A

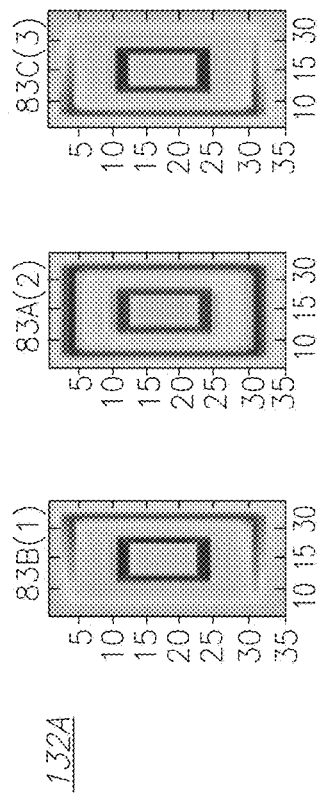
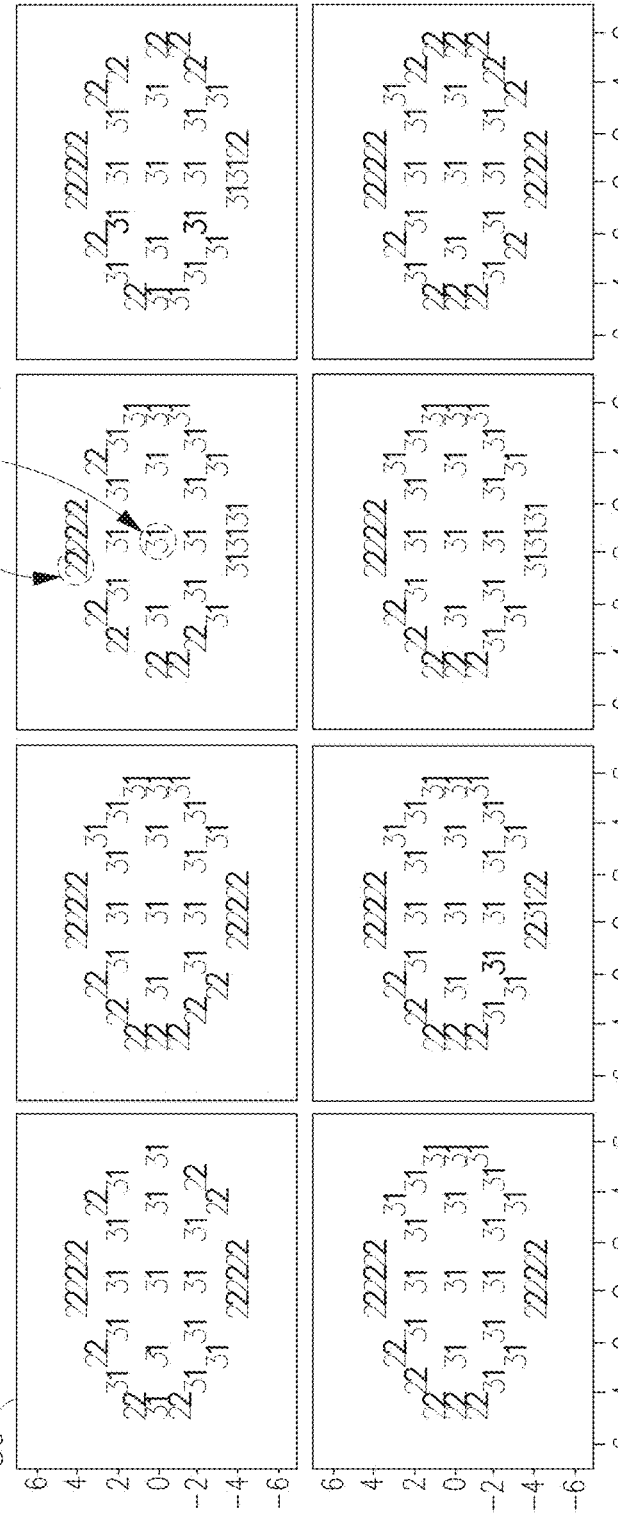

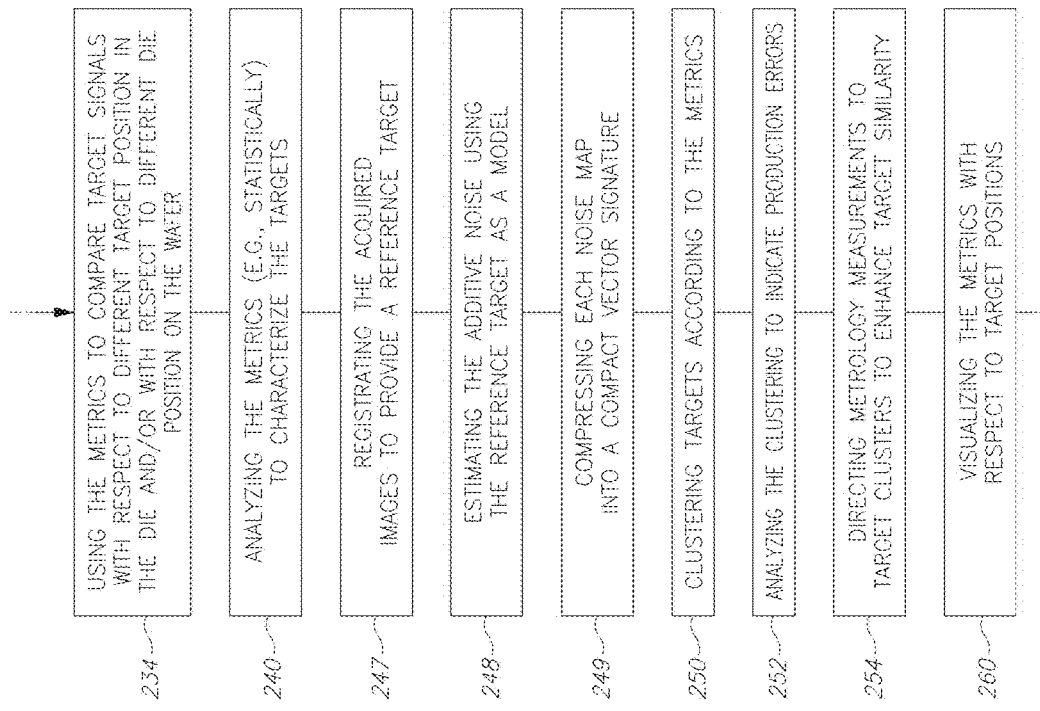
Figure 5 (cont. 1)

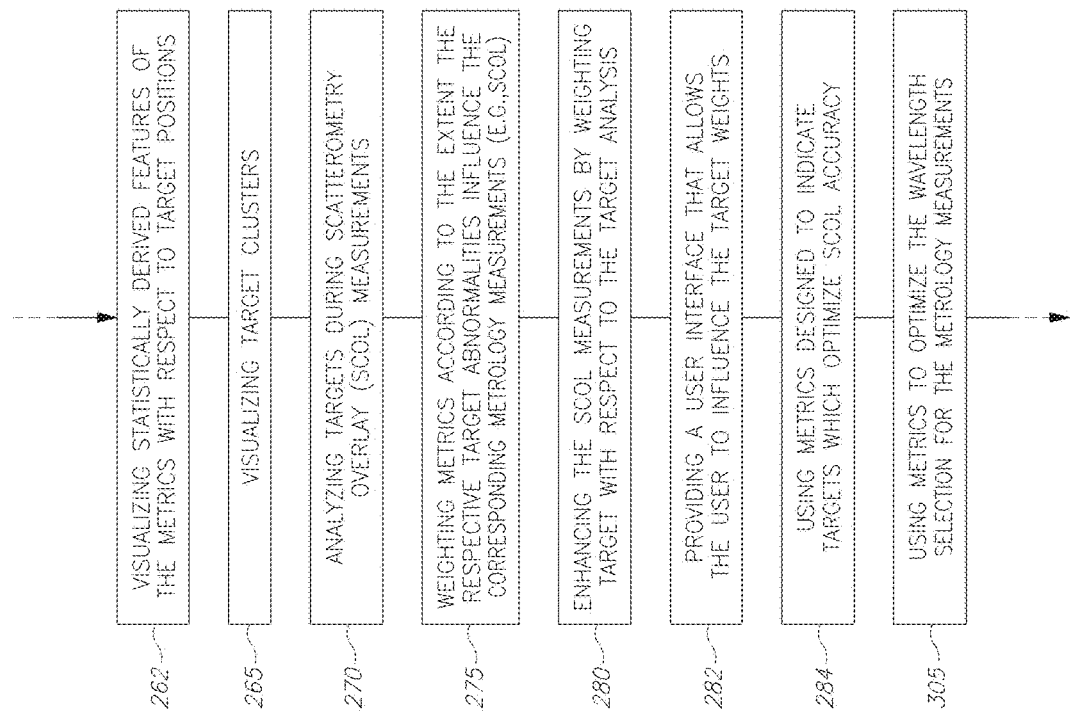
Figure 5 (cont. 2)

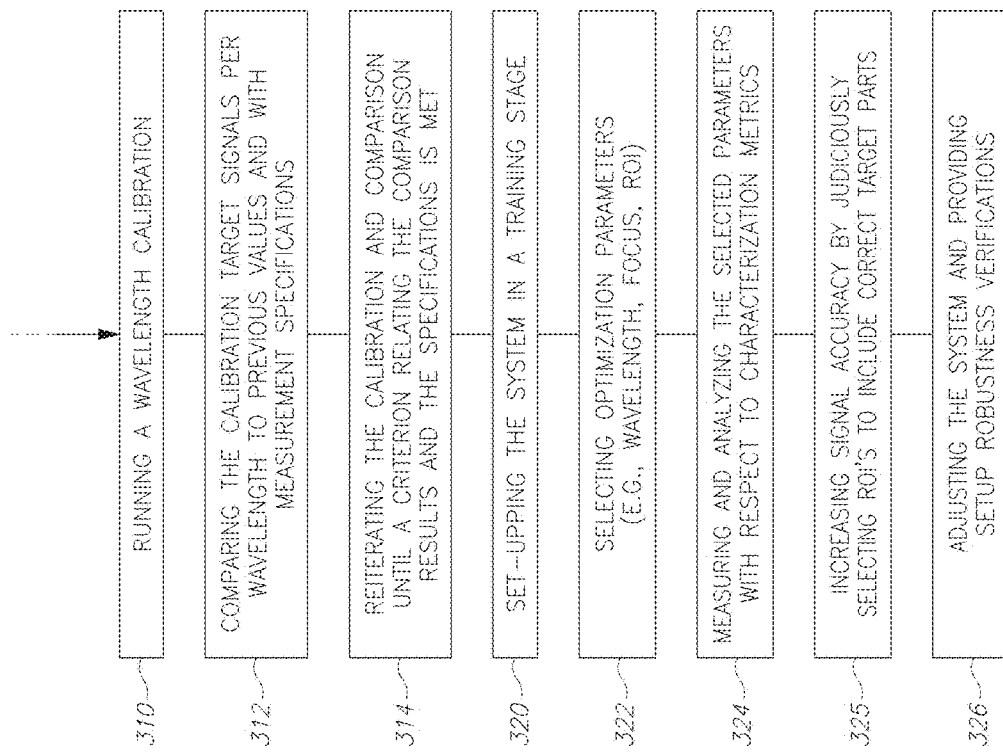
Figure 5 (cont. 3)

METHOD, SYSTEM, AND USER INTERFACE FOR METROLOGY TARGET CHARACTERIZATION

CROSS-REFERENCE TO RELATED APPLICATIONS

This application is filed under 35 U.S.C. § 120 and § 365(c) as a continuation of PCT International Patent Application No. PCT/US2013/069263, filed Nov. 8, 2013, which application claims the benefit under 35 U.S.C. 119(e) of U.S. Provisional Patent Application No. 61/724,846, filed Nov. 9, 2012, which applications are incorporated herein by reference in their entirety.

BACKGROUND OF THE INVENTION

1. Technical Field

The present invention relates to the field of metrology, and more particularly, to characterization of metrology targets.

2. Discussion of Related Art

Metrology measurements are very accurate measurements of metrology targets produced on wafers, used to identify and quantify errors and inaccuracy in semiconductor devices. Various methods are used to measure overlay (OVL) between produced layers and various algorithms are used to estimate errors and inaccuracies of the production process and of the metrology measurements themselves. Examples include regression methods based on maximum OVL values, optimization of the weighted OVL calculations, optical methods, noise reduction methods, and recipe optimization.

Exemplary approaches, which are incorporated herein by reference in their entirety, are taught by WIPO Publication No. 2013092106, disclosing producing an elaborate sampling plan having sub-sampling plans which are constrained to a predetermined fixed number of measurement points and is used to control an inspection apparatus; U.S. Pat. No. 8,525,993 disclosing the use of asymmetry metrology that uses the off-diagonal elements of a Mueller matrix calculated using a rigorous electromagnetic model; and Raymond, C. J. 2011, "Improved overlay control using robust outlier removal methods", Proc. SPIE 7971, Metrology, Inspection, and Process Control for Microlithography XXV, 79711 G, disclosing regression based outlier removal methods.

SUMMARY OF THE INVENTION

One aspect of the present invention provides methods and systems which identify specified metrology target abnormalities using selected metrics and classify the identified target abnormalities geometrically to link them to corresponding sources of error. Identification may be carried out by deriving target signals from corresponding targets on a wafer, calculating the metrics from the target signals using respective functions and analyzing the metrics to characterize the targets.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIGS. 2A-2C illustrate examples for kernels taken from different targets and exhibiting features used to characterize targets, according to some embodiments of the invention.

FIGS. 2D-2F illustrate examples for kernels taken from different targets and visualizations of the distribution of targets' metrics over a wafer, according to some embodiments of the invention.

FIG. 2G illustrates multiple kernels which were derived at different wavelength ranges, identified as different colors, in a non-limiting example, according to some embodiments of the invention.

FIG. 2H illustrates kernels of two target elements with an indication for the preferred ROI selection, in a non-limiting example, according to some embodiments of the invention.

FIGS. 2I and 2J illustrate kernels from SCOL targets, in a non-limiting example, according to some embodiments of the invention.

FIGS. 3A and 3B illustrate schematically a metric for estimating ROI divergence, according to some embodiments of the invention.

FIGS. 4A and 4B are high level schematic illustrations of target clustering and cluster visualization, according to some embodiments of the invention.

DETAILED DESCRIPTION OF THE INVENTION

Figure 1A:
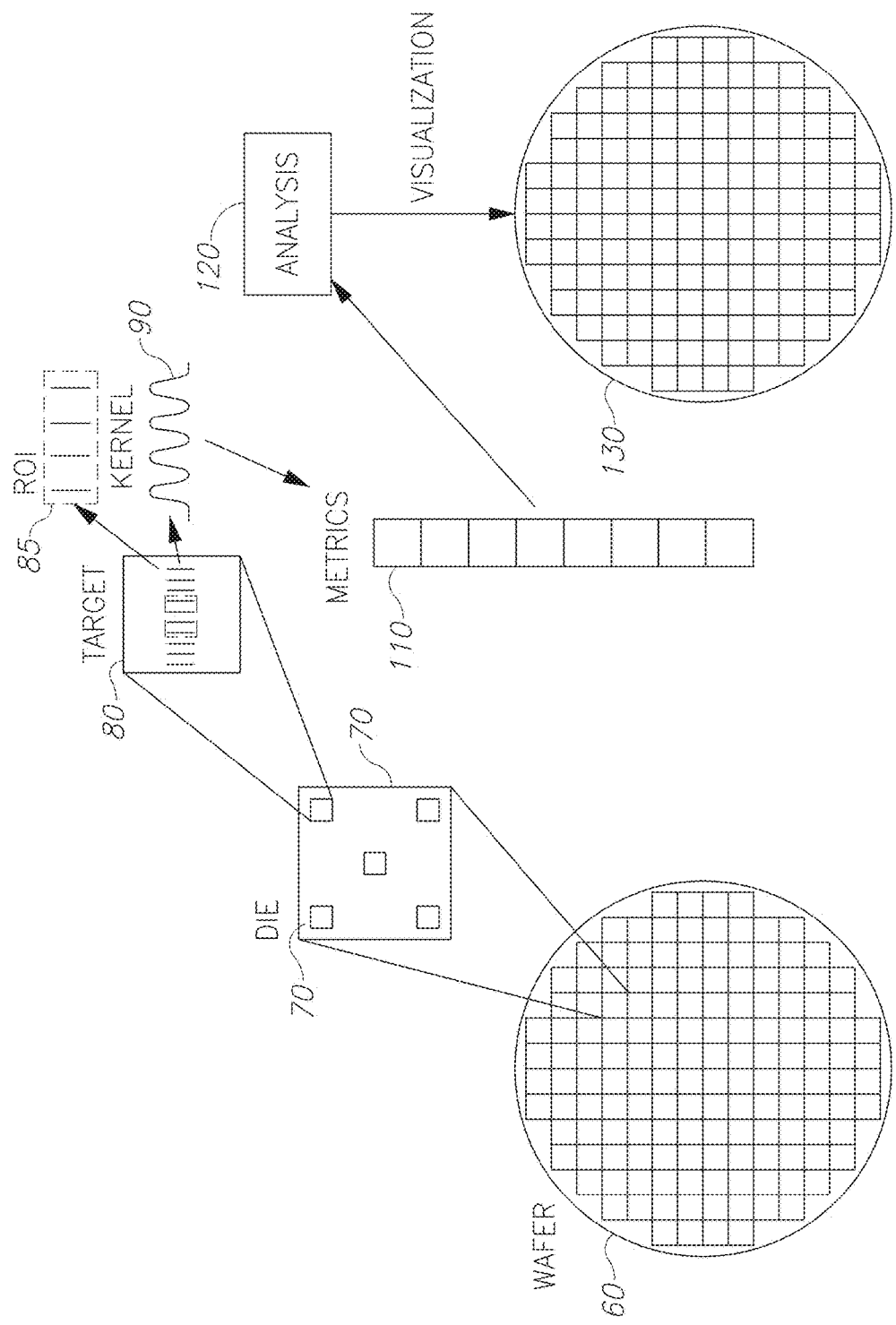
FIG. 1A is a high level schematic block diagram of a metrology process according to some embodiments of the invention.

Prior to the detailed description being set forth, it may be helpful to set forth definitions of certain terms that will be used hereinafter.

The terms "target" or "metrology target" as used in this application refer to a region from which metrology information is extracted. Metrology targets may be positioned on dedicated areas on the chip, on device edges or within the device area. The term "target" may relate to periodic structures as well as to non-periodic structures.

The term "target signal" as used in this application refers to measurement data, projections or images of the target, which are derived from the target. The target signal may have the same number of dimensions as the target (e.g., comprise a partial or full image of the target) or have less dimensions than the target (e.g., comprise a one dimensional section of the target). The term "target signal" may refer to any type of target-related raw data and may be taken from any part of the target and its immediate vicinity. For example, the term "target signal" may include spectral data relating to the target and pupil images of the target.

The term "region of interest (ROI)" as used in this application refers to a selected area of a target (possibly extending to the immediate vicinity of a target) which is used to derive measurement data or images of the target.

The term "kernel" as used in this application refers to a lower dimension projection of the target, for example a cross section of the target along the ROI. The term "kernel" is used in this application as a non-limiting example for a target signal. In cases of targets or target parts which are variable along a first direction and not variable along a second (commonly orthogonal) direction, the term "kernel" refers to a projection along the first direction and the term "ortho-kernel" refers to a projection along the second direction.

The term "metric" as used in this application refers to a value or a set of values which are derived with respect to the target signal or a kernel derived therefrom according to a specified procedure, usually the application of a certain mathematical function or algorithmic procedure. Without being bound to theory, metrics are used to quantify specific features of the targets, the target signals or the kernels derived from the targets. Metrics may relate to one target or to several targets, and may relate to one part of the target or to several parts of the targets (e.g., parts of the targets at the same or at different layers). Metrics may also relate to other metrics, e.g. reflect statistical functions applied to a specified group of metrics over a specified group of targets.

The terms "visualization", "presentation" or "signature" as used in this application refer to an image of data relating to the targets, target signals and/or kernels derived from them. Such data may be visualized in a raw state, may be related to one or more metrics, may include statistical analysis of several metrics and/or may relate to a clustering of targets and the relation of individual targets to such clustering. The visualization may (but may not) be carried out with respect to the spatial arrangement of dies on the wafer and/or with respect to the spatial arrangement of the targets in the dies.

The term "clustering" as used in this application refers to a grouping of targets according to specified criterions, e.g. clustering of the targets in an n-dimensional space defined by certain n metrics. Clustering may be carried out by any clustering algorithms (deterministic or heuristic), in a non-limiting example by unsupervised machine learning techniques.

The term "scatterometry overlay (SCOL)" as used in this application refers to a metrology method that derives metrology information from the phases of diffraction orders (e.g. the +1 and −1 diffraction orders) that reflect off targets which contain periodic structures such as gratings or grating cells.

The terms "die" or "field" as used in this application refer to a well-defined area on a wafer which includes electronic circuitry as device(s) as well as metrology targets. Multiple dies are arranged on a wafer.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1B:
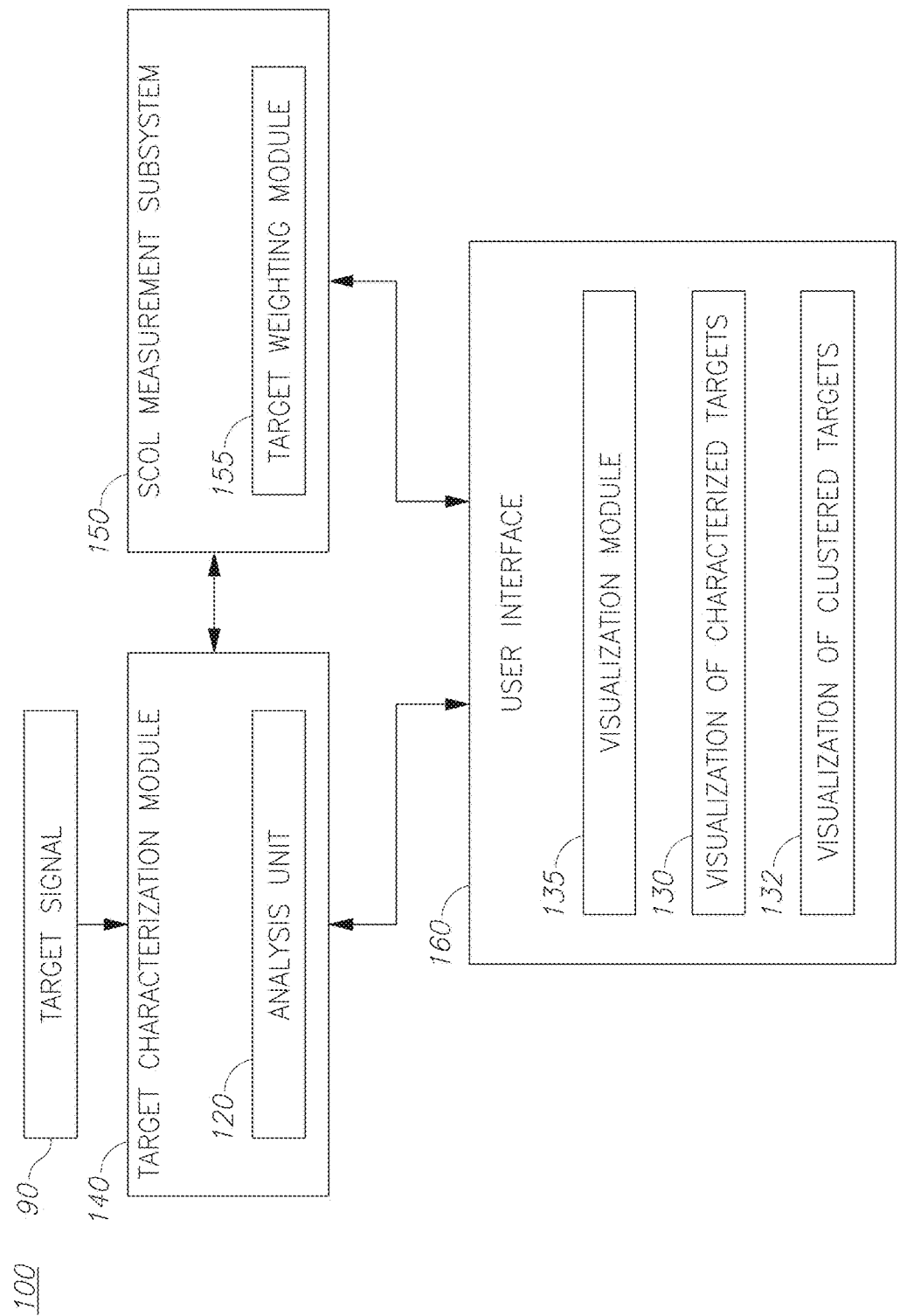
FIG. 1B is a high level schematic block diagram of a metrology system according to some embodiments of the invention.

FIG. 1A is a high level schematic block diagram of a metrology process according to some embodiments of the invention. The metrology process analyses metrology targets 80 in dies 70 applied to a wafer 60, as explained in the following. FIG. 1B is a high level schematic block diagram of a metrology system 100 according to some embodiments of the invention. Metrology system 100 comprises a target characterization module 140 arranged to derive a plurality of target signals 90 (e.g., kernels 90 from specified regions of interest 85 (ROIs)) from corresponding targets 80 on wafer 60. Kernels 90 comprise quantitative data relating to ROI 85 in target 80, for example kernel 90 may comprise a cross section of ROI 85, illustrated schematically in FIG. 1A.

Target characterization module 140 may be further arranged to calculate at least one specified metric 110 from the measured target signals 90 using respective functions, and to analyze (e.g., via analysis unit 120) metric(s) 110 to characterize the targets. In certain embodiments, target characterization module 140 is arranged to characterize targets 80 by a statistical analysis of a plurality of specified metrics 110. Metrics 110 may be selected to quantify target regularity, target asymmetry and/or ROI position in the target, and thereby be used to identify exceptional targets 80 and/or divergent ROIs 85, as exemplified below. Metrics 110 may be selected to identify outliers, i.e., targets which diverge extremely (e.g., several σ's from the target model), and these outliers may then be removed from the measurement process.

In certain embodiments, multiple target signals (e.g., kernels 90) may be derived from different parts of each target 80, such as target elements on different layers, inner and outer target elements etc. The analysis described below may compare target signals 90 from different parts of targets 80, and appropriate metrics 110 may be applied to identify abnormalities within targets 80. For example, metric 110 may be a white noise metric used to quantify a level of randomness in the target signal. Such metric can be taken to indicate the target signal's level of complexity and thus imply the structural regularity of target 80 in ROI 85.

In certain embodiments, metrics 110 may be selected to identify any one of a range of target abnormalities and to classify target abnormalities geometrically. The geometrical classification may be used to link each type of target abnormality with a corresponding source of error, and eventually correcting for the error, computationally or by correcting the process. Metrics 110 may be used to identify error sources which are either algorithmic in nature or which result from process errors and biases. Thus, system 100 may provide an additional metrology layer, e.g., beyond a SCOL procedure, for detecting process errors. Moreover, system 100 may effectively provide a wafer overview, as illustrated below. In certain embodiments, a plurality of metrics 110 may be weighted according to the extent the respective target abnormality influences the corresponding metrology measurements. For example, metrics may be weighted according to the influences of the respective target abnormalities on SCOL measurements. In certain embodiments, metrics 110 may be specifically constructed or combined to identify, or catch, predefined features. Such features may comprise target abnormalities but may also be related to the measurement process (see, e.g., the $\Delta_2$ metric presented below, which was design to catch ROI dislocation), to performed algorithms and other parts of the production and metrology processes.

In certain embodiments, target characterization module 140 is arranged to identify target signals 90 which diverge from other target signals (according to any or some of metrics 110) and remove or down-weight these targets from the metrology process. A statistical analysis may be applied to define the targets that are to be removed and/or the weights given to these targets.

In certain embodiments, metrics 110 may be defined for any target signal 90 of target 80. For example, target signals 90 maybe defined in two dimensions of target 80 (e.g., x and y axes) or in any direction across target 80. Metrics 110 may be defined to refer to more than one target signal 90 related to target 80, e.g., to combine measurements from the x and y directions of target 80.

Certain embodiments comprise a scatterometry overlay (SCOL) metrology system, comprising target characterization module 140, at least partly embedded in computer hardware, and arranged to identify specified metrology target abnormalities using a plurality of selected metrics 110; classify the identified target abnormalities geometrically; link the geometrically classified target abnormalities to corresponding sources of error; indicate the sources of errors; and enhance SCOL measurements by weighting metrology targets using the selected metrics. Target characterization module 140 may be arranged to identify the target abnormalities by deriving a plurality of target signals 90 (e.g., kernels 90 from specified regions of interest (ROIs) 85) from corresponding targets 80 on wafer 60 and measuring the selected metrics from target signals 90 using respective functions (see examples below). The SCOL system may comprise an analysis unit 120 arranged to perform a statistical analysis of metrics 110 to enhance the classifying and the linking. The analysis may be performed by target characterization module 140 or by analysis unit 120 embedded therewithin. Target characterization module 140 may be further arranged to cluster targets 80 according to selected metrics 110 to analyze the clustering to indicate the sources of errors and/or to direct metrology measurements to target clusters to enhance target similarity. The SCOL system may comprise visualization module 135 arranged to visually present the geometrical classification (130), to visualize the statistical analysis of the metrics (135) and/or to visualize the clustering (132). In certain embodiments, imaging equipment may be used according to the suggested methods to enhance scatterometry target inspection. Alternatively or additionally, the SCOL equipment maybe used to obtain the raw signal data.

In certain embodiments, the invention characterizes and classifies raw measurements (target signals), for example: kernels, spectra and pupil images; which are used for overlay (OVL) measurement. The methods and systems may identify outliers (exceptional targets) and clusters of raw measurements which may be used to improve OVL measurements and OVL modeling (for example, to improve TMU (Total Measurement Uncertainty), correctables and residuals) as well as optimize the selection of illumination wavelengths, focus, zone patterns (in sub areas of the wafer), field patterns (in specific dies) and ROI selection. In certain embodiments, target ROI selection may be carried out during measurement in real time. The methods and systems may be applied during recipe train, run (measurement), tool calibration, and also in post process analysis.

FIGS. 2A-2C illustrate examples for kernels 90 taken from different targets 80 and exhibiting features used to characterize targets, according to some embodiments of the invention. Kernels 90A were derived from regular targets 80 while kernels 90B were derived from deficient (abnormal) targets. Arrows indicate parts of the kernels which differ between kernels 90A, 90B and indicate these abnormalities. Illustrated kernels 90 are periodic (periodic kernels 90 are presented as non-limiting examples, as kernels 90 may comprise non-periodic raw target signals as well), and metric 110 applied to them in the illustrative example is the white noise metric Fisher's Kappa.

FIGS. 2A and 2B illustrate kernels 90A, 90B from different positions in die 70. Kernel 90A represents kernels from targets at various positions, while kernel 90B represents targets from one position in the die, in a non-limiting example. Fisher's Kappa metric ranges between 90 and 120 for kernels 90A at different positions and dies, and ranges between 25 and 45 for kernels 90B at different dies. Thus, this metric can be effectively used to distinguish these two types of kernels, kernel 90B indicating a defective target. Possibly, targets 80 which produce kernels 90B may be down weighted or removed from the metrology measurements, or may be corrected algorithmically or via process changes. Various measures may be used to quantify target handling for optimizing the metrology measurements.

Kernels 90 from targets 80 may be compared (using metrics 110) with respect to different target positions in die 70 (field analysis) and/or with respect to different die positions on wafer 60 (zone analysis). The latter analysis may be used to identify production process errors such as errors relating to track modules, deposition, etch process, etc. Specific metrics 110 may be used to identify the specific source of error according to its typical pattern of target errors.

FIG. 2C illustrates kernel 90A of targets which are correctly centered and kernel 90B of targets which are incorrectly centered (the arrow indicates a tail in kernel 90B which indicates that ROI 85 is extended beyond the actual target structures), in a non-limiting example. Such kernels 90B indicate either an error in target positioning or a misplaced ROI 85. In both cases, the error may be identified by a corresponding metric 110 and corrected (or target 80 may be discarded from the calculations).

In certain embodiments, target characterization module 140 may comprise a database of metrics 110, extracted from target images and designed to reflect on the target appearance with respect to an ideal target, regarding, for example, target symmetry, target periodicity, target uniformity, noise levels, etc. Some metrics 110 may be computed based on one dimensional information (e.g., a kernel, an ortho-kernel), while other metrics 110 may use two dimensional information (e.g., ROIs 85 or whole target regions as target signals 90).

In certain embodiments, metrics 110 may be used directly to indicate target characteristics or aberrations. In certain embodiments, interrelations between metrics relating to the same targets may be used to indicate target characteristics. In certain embodiments, visualization 130 of metrics 110 with respect to whole wafer 60 or with respect to a specified set of targets 80, termed "metric signature", may be used to characterize the targets.

Metrics 110 may be selected to quantify any desired target feature, such as target symmetry (e.g., for box in box targets), target declination in any direction (e.g. x and y directions relating to the kernel and ortho-kernel respectively), relative location of ROI 85 with respect to target 80, statistical target measures, such as averages and standard deviations of target images or partial images, statistical measures relating to Fourier-transformed target signals (e.g., kernels or images), relating e.g., to moments of the Fourier harmonics, various precision measurements, measures quantifying target noise, self-correlations between targets and parts of targets at the same or at different layers, metrics relating to components of the target signals (e.g., periodic components, linear components and noise components) and so forth.

Metric signatures may relate to values of various metrics, to values relating to combination of metrics, to values relating to a statistical analysis of one or more metrics, or to values relating to metrics that are calculated when different measurement parameters are changed (e.g., different illumination).

In certain embodiments, metrology system 100 further comprises a visualization module 135 (FIG. 1B) arranged to visually present (130) metric(s) 110 with respect to target positions on wafer 60. For example, presentation 130 may comprise values (e.g. color coded) of the metrics for targets 80 in each die 70 in the corresponding position of die 70 on wafer 60.

Figure 2D:
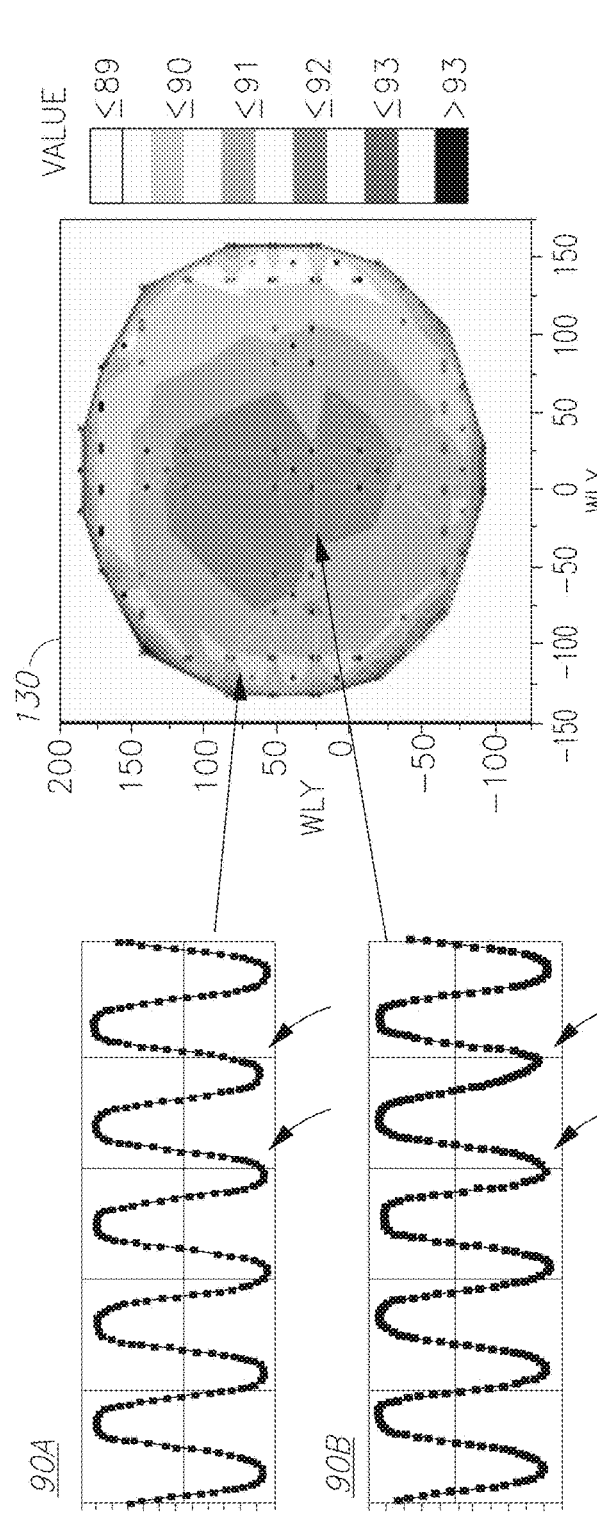
Figure 2E:
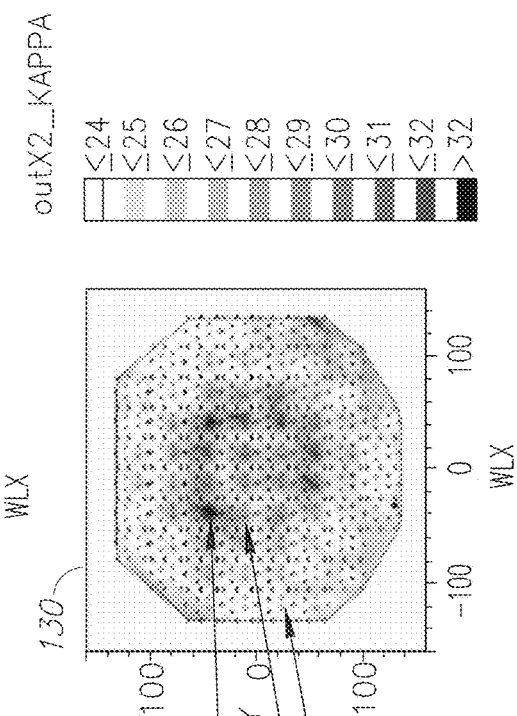

FIGS. 2D-2F illustrate examples for kernels 90 taken from different targets 80 and visualizations 130 of the distribution of targets' metrics over wafer 60, according to some embodiments of the invention.

FIG. 2D illustrates kernel 90B characteristic of an over-etched target in comparison to kernel 90A of a correctly etched target, in a non-limiting example. Metric 110 such as Fisher's Kappa identifies this difference (κ values≤90 for correctly etched targets corresponding to kernel 90A and κ values>90 for incorrectly etched targets corresponding to kernel 90B). Visualization 130 may be configured to provide a wafer wide overview of metric 110 with respect to some or all targets 80, which thus indicates visually the distribution of over-etching on wafer 60. Visualization 130 may thus be used to correct the etching process and/or to correct the metrology results to relate differently to correctly and incorrectly etched target.

FIG. 2E illustrates kernels 90A, 90B, 90C from different positions in wafer 60 and corresponding visualization 130, in a non-limiting example. The kernels have different metric values, e.g., kernel 90A corresponds to high κ values (larger than 32), kernel 90B corresponds to intermediate κ values (around 28), kernel 90C corresponds to low κ values (smaller than 24), indicating low quality targets. In certain embodiments, wafer edge effects, resulting in defective targets being produced on wafer edges, may be easily detected using visualization 130 to distinguish defective targets having lower κ values from correctly produced targets having high κ values above.

FIG. 2F illustrates visualizations 130 of Fisher's Kappa metric 110 over wafer 60, separated with respect to inner target elements in the current layer, and to outer target elements in the previous layer, in a non-limiting example. Clearly, different target errors are associated with these partial structures, and these may be corrected in production or algorithmically.

, may be used to optimize the wavelength selection for the metrology measurements. The wavelength selection methodology may be based on kernel analysis integrated with target noise calculation and continuity. In certain embodiments, appropriate wavelengths may be selected to reduce target noise. FIG. 2G illustrates multiple kernels 90 which were derived at difference wavelength ranges, identified as different colors, in a non-limiting example. The disclosed characterization, analysis and optimization considerations may be applied to kernels 90 derived using different wavelength ranges and be used to select and optimize the imaging illumination. For example, in the illustrated example, the kernels derived at different illumination conditions exhibit different features with respect to their constancy, stability, contrast etc. Metrics 110 may be used to quantify target signals 90 under different illumination conditions and allow selecting the best illumination conditions according to criteria such as kernel stability and high accuracy. In the illustrated example, the "lime" illumination is superior due to its combination of high stability and accuracy.

In certain embodiments, system 100 may apply a calibration procedure which comprises running a wavelength calibration, comparing the calibration kernel per wavelength to previous values, and adjusting the wavelengths (e.g., iteratively) if results do not satisfy specified requirements. In certain embodiments, system 100 may apply an optimization procedure comprises choosing optimization parameter sets (e.g. wavelength, focus, ROI, etc.), measuring the optimization parameters and corresponding metrics to define an optimal setup and verify its robustness to fluctuations. In certain embodiments, during measurements, system 100 may check the targets with respect to their asymmetry, or any other characteristic, and if needed apply a recovery procedure (optionally including clustering) or dismiss the measurement.

FIG. 2H illustrates kernels 90 of two target elements (e.g. belonging to different layers, namely the upper current layer and the lower previous layer) with an indication for the preferred ROI selection, in a non-limiting example. Thus, system 100 allows increasing signal accuracy by selecting ROI's 85 judiciously to include parts of target 80 which are produced correctly, including optimizing ROI 85 with relation to different target layers. In certain embodiments, target characterization module 140 may be arranged to optimize ROI 85 with respect to kernels 90, e.g., using metrics 110. In the illustrated case, kernels 90 may be analyzed separately, with respect to irregularities in each layer, and the optimal ROI may be selected under considerations with respect to both layers.

FIGS. 2I and 2J illustrate kernels 90 from SCOL targets, in a non-limiting example. FIG. 2I illustrates kernel 90A of a correctly produced SCOL target, and kernel 90B of an incorrectly produced SCOL target. The inventors have found out that the presented methods and system enable to characterize SCOL targets, in spite of their typical fine segmentation. Such characterization is particularly efficient for the current (upper) layer, and may be used e.g., to detect components of the targets (e.g., periodic, linear or noise components) and correct them computationally or with respect to the process. FIG. 2J illustrates a kernel that exhibits a defective sub-area (arrow) which is not uniform with the rest of the SCOL target and may be used to indicate a particle on the wafer. Thus, target characterization may include validation of regions in the target or between targets.

Figure 2K:
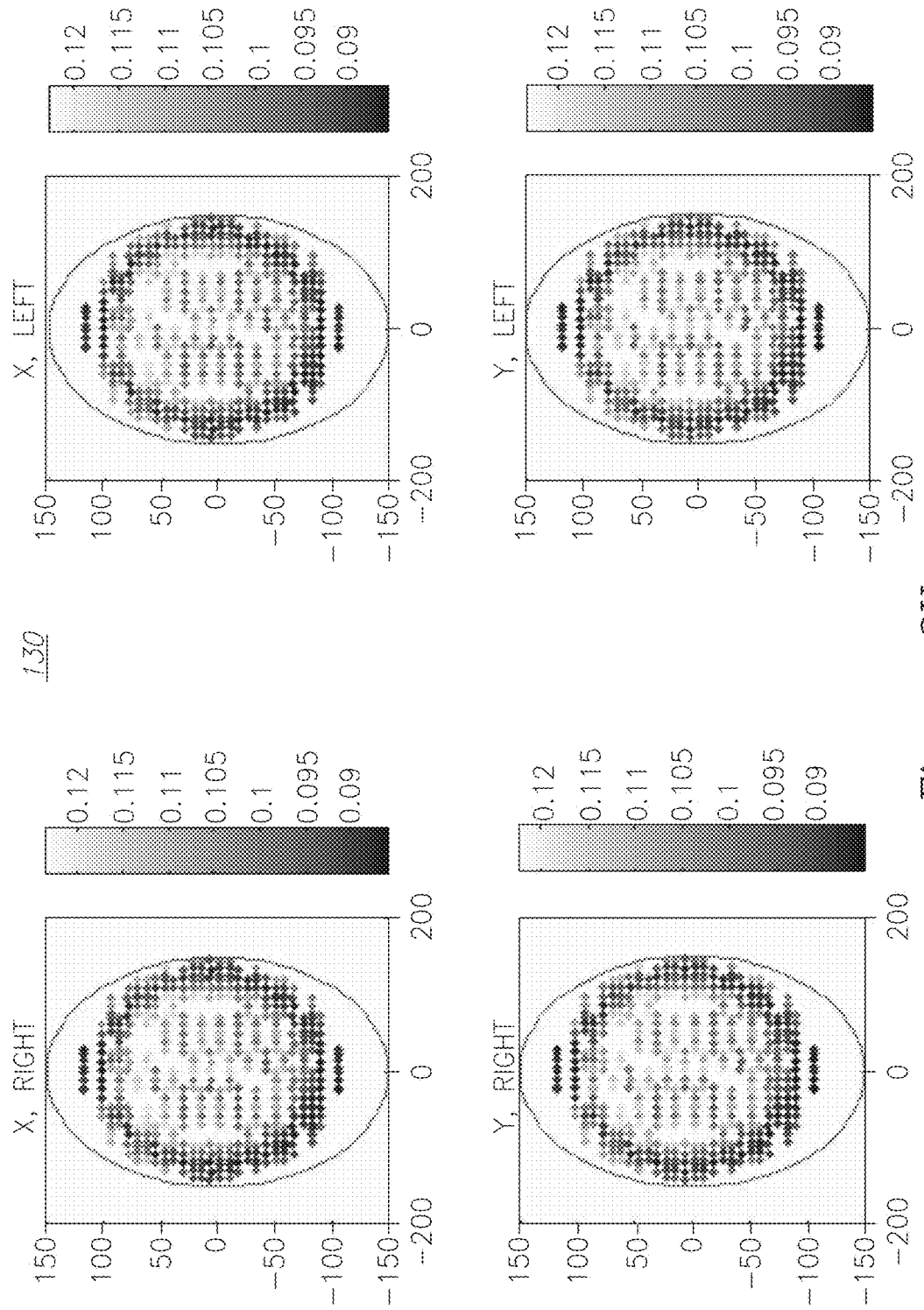
FIG. 2K illustrates a visualization of a kernel precision metric for different parts of the target, in two directions, in a non-limiting example.

FIG. 2K illustrates a visualization of a kernel precision metric for different parts of the target, in two directions, in a non-limiting example. Kernel precision metric 110 may be defined, in a non-limiting example, as a self-correlation of a target part, with or without rotation. FIG. 2K is an exemplary illustration of such metric 110 with respect to two regions in target 80, namely a left region and a right region of a box in box target, measured in two directions, denoted x and y. The figure illustrates that different target characteristics can be identified and are consistent with respect to their positions on the wafer.

Figure 2L:
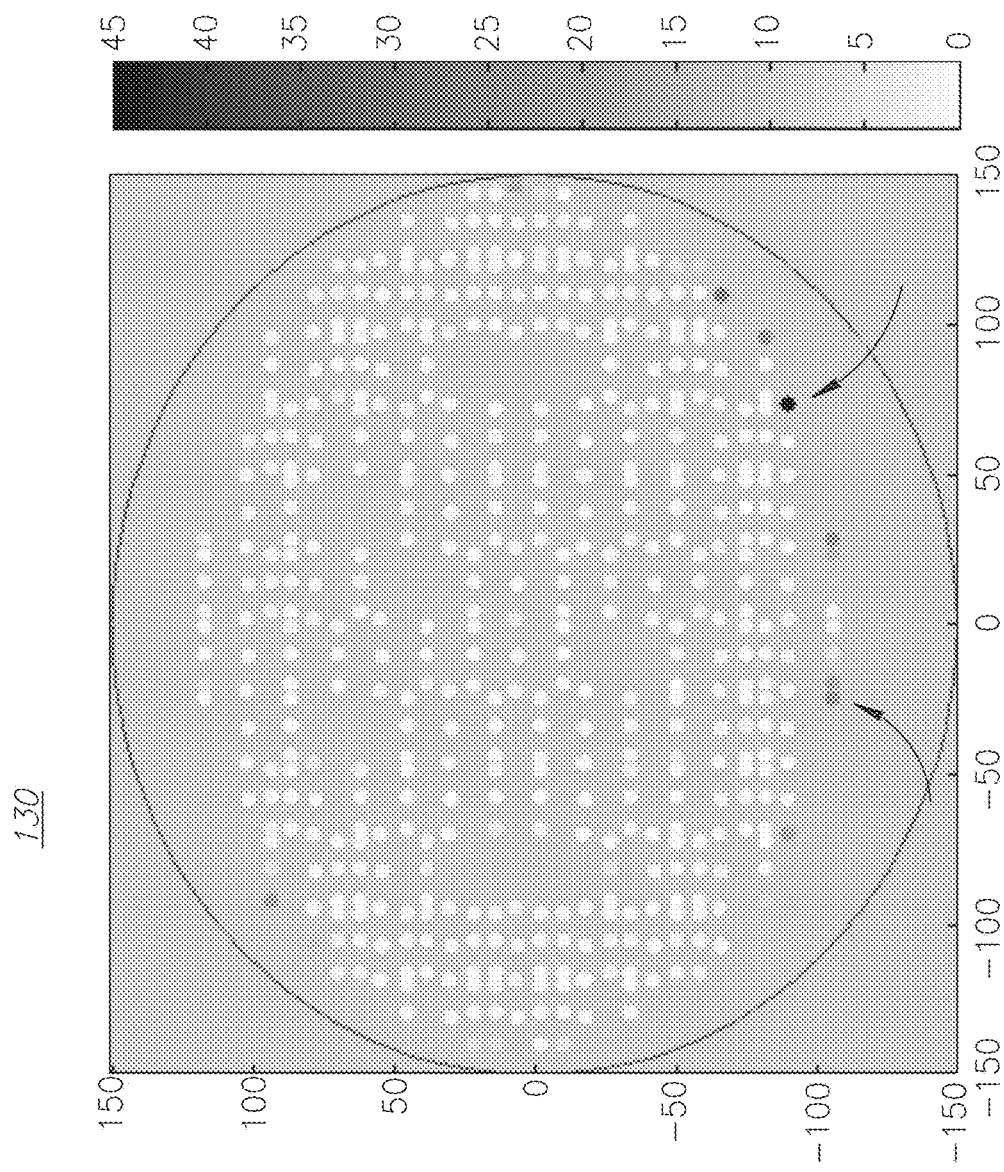
FIG. 2L illustrates a visualization of a statistical analysis of multiple metrics for outlier detection, in a non-limiting example.

FIG. 2L illustrates visualization 130 of a statistical analysis of multiple metrics for outlier detection, in a non-limiting example. The dot in each target location indicates a number of metrics 110 which indicate the respective target as an outlier. Targets that are indicated by arrows are ones that are exceptional with respect to a large number of metrics 110. Outlier targets may be removed from the metrology measurements, or targets may be weighted according to the number of metrics which indicate them as outliers.

Figure 2M:
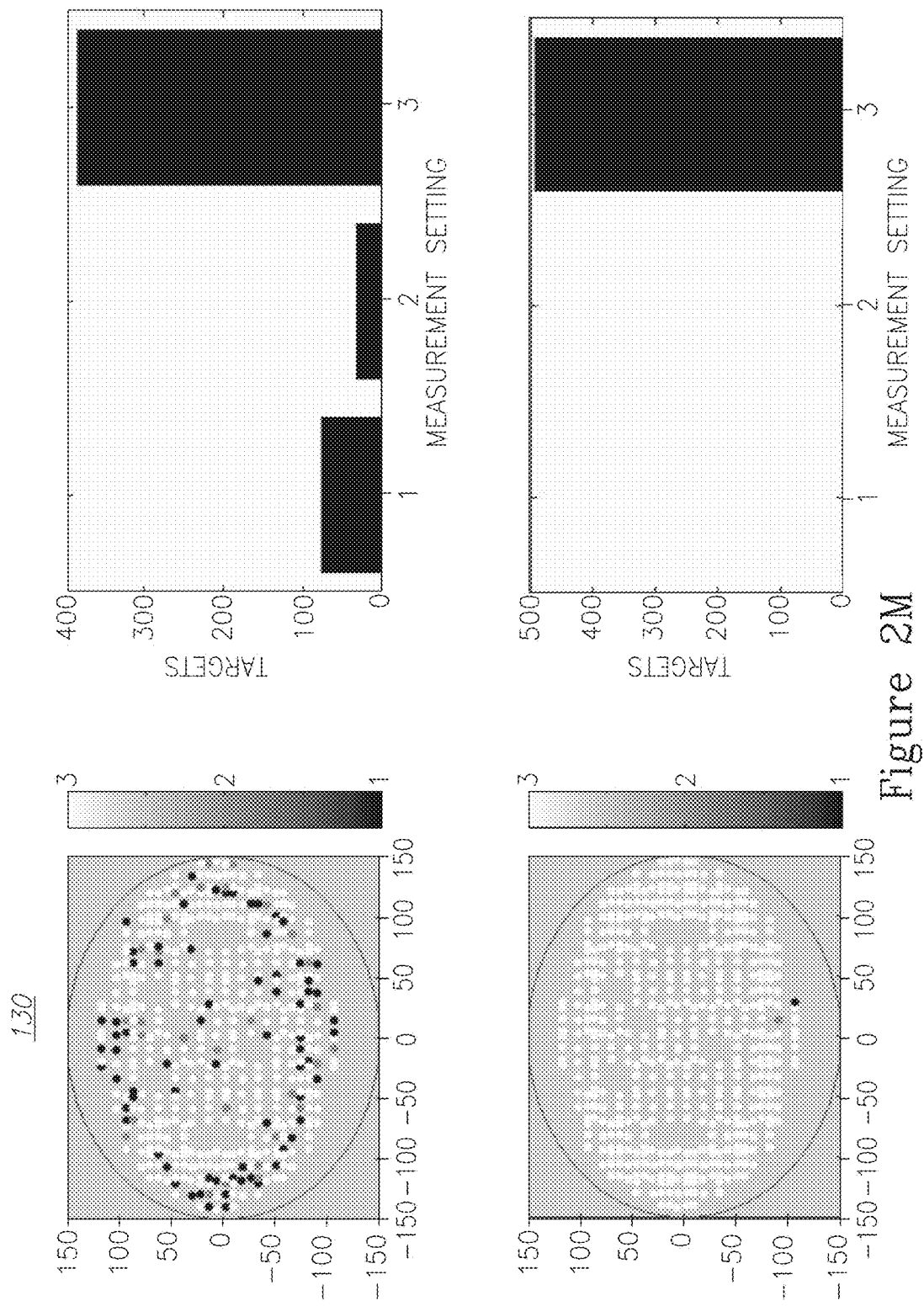
FIG. 2M illustrates comparisons of measurement settings using visualization and statistical analysis, in a non-limiting example.

FIG. 2M illustrates comparisons of measurement settings using visualization and statistical analysis, in a non-limiting example. The figure illustrates a comparison of three measurement settings (denoted 1, 2 and 3). Visualizations 130 illustrate for each target, which measurement setting yielded the best metric value (using in this non-limiting example the self-correlation metric presented above). Upper visualizations 130 present measurement in one (x) direction, lower visualizations 130 present measurement in another (y) direction. FIG. 2M further illustrates an elementary statistical analysis (histograms, which clearly can be elaborated to include, e.g., measurements of additional metrics, target weights, clustering, etc.) of the targets with respect to the measurement settings, namely the number of targets which are most accurately measured for each measurement setting. Such analysis allows selecting optimal measurement settings (as an elaboration to illumination conditions presented above) and furthermore, can be used to map the targets (spatial location on the wafer) with respect to specific measurement settings, allowing their weighting, clustering, etc.

In certain embodiments, visualization 130 of a noise metric over the wafer may comprise a dot in each target location that indicates a value of a noise metric. The overall noise pattern may be used to indicate various production phenomena. As non-limiting examples, the inventors have identified noise patterns like: a directional increase or decrease of the noise across the wafer, differences between a central region on the wafer and its periphery, enhanced target noise in one of the layers, and local noise patterns.

Figure 3B:
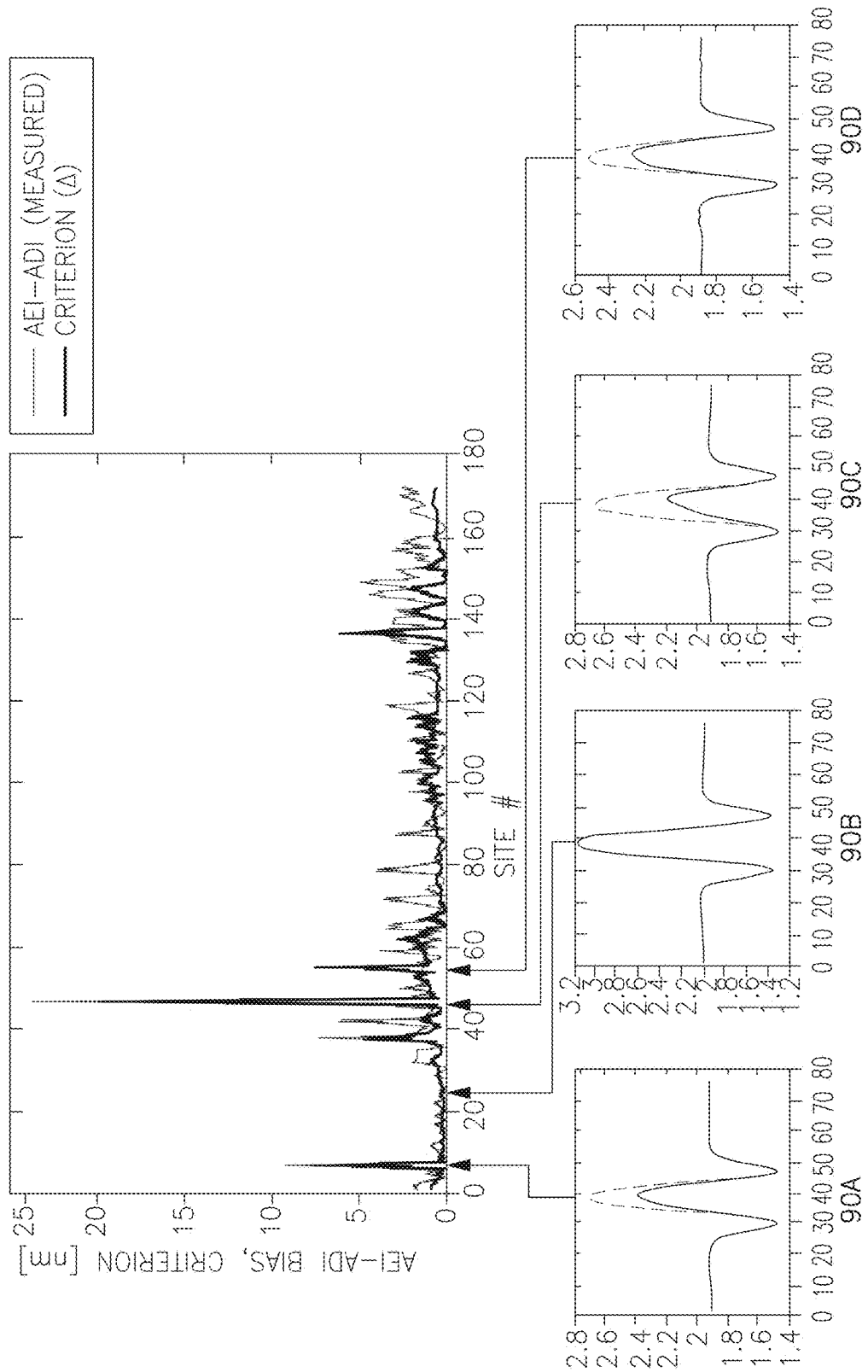

FIGS. 3A and 3B illustrate schematically a metric for estimating ROI divergence, according to some embodiments of the invention. The metric quantitatively estimates the effect of target asymmetry on the accuracy of overlay measurements.

A perfectly symmetric target can be described by a function f(x) with a center of symmetry at point $x_0$, so that $f(x-x_0)=f(x_0-x)$. In this case the Fourier transform of the signal yields $F(\omega)=e^{i\omega x_0}\cdot\Psi(\omega)$, where $\Psi(\omega)$ is a real function. This expression is correct for a discrete Fourier transform performed on bounded range or when $x_0$ is an exact center of the range or when the derivatives of f(x) at the ends of the range are zero and f(0)=f(end). In the case of a box in box target, this is the case and if there is a problem with the last condition it can be easily fixed. It follows that the phase of the symmetric signal $F(\omega)$ behaves linearly with $\omega$ with a slope proportional to the deviation of the ROI center from the target center and any deviation from such behavior indicates the target asymmetry. FIG. 3A schematically illustrates the target function f(x) as line 81, centered at the center of target 80, from which the center of the ROI 85 is offset by $\Delta x$. FIG. 3A schematically illustrates the Fourier transformed $F(\omega)$ 82 with the averaged slope at angle $\delta$ to the $\omega$ axis and the deviating function $\Psi(\omega)$, representing the target asymmetry, bound within a range $\Delta$ with respect to angle $\delta$. $\Delta$ thus provides a measure for the target asymmetry. It is noted that angle $\delta$ provides a direct estimate of $\Delta x$ in nm, which is an intuitive metric for the deviation of the ROI center from the target center. To calculate $\delta$ and $\Delta$, the following development is presented.

Since f(x) is a real function it can be presented as:

$$f(x_n) = a_0 + 2\sum_{k=1}^{N} a_k \cdot \cos\left(\frac{2\pi k}{N} x_n + \phi_k\right)$$

Here N is the number of pixels in the ROI and the correspondent number of harmonics obtained by FFT (fast Fourier transform). Let us define the cross-correlation function $$\Pi(\delta) = \sum_{v=1}^{N} f(v) \cdot f(N - v + 1 - \delta)$$

$$\Pi(\delta) = \sum_{v=1}^{N} \left[a_0 + 2\sum_{k=1}^{N} a_k \cdot \cos\left(\frac{2\pi k}{N}v + \phi_k\right)\right] \cdot$$

$$\left[a_0 + 2\sum_{t=1}^{N} a_t \cdot \cos\left(\frac{2\pi k}{N}(-v + 1 - \delta) + \phi_t\right)\right] =$$

$$= N \cdot a_0^2 + 4\sum_{k=1}^{N} a_k^2 \cdot \sum_{v=1}^{N} \cos\left(\frac{2\pi k}{N}v + \phi_k\right) \cdot$$

$$\cos\left[\frac{2\pi k}{N}(-v + 1 - \delta) + \phi_k\right] =$$

$$= N \cdot a_0^2 + 2N \cdot \sum_{k=1}^{N} a_k^2 \cdot \cos\left[\frac{2\pi k}{N}(1 - \delta) + 2\phi_k\right]$$

The position of center of symmetry $\delta$ corresponds to the maximum of cross-correlation function and can be found by equating the derivative of cross-correlation function to zero, i.e.:

$$\sum_{k=1}^{N} k \cdot a_k^2 \cdot \sin\left[\frac{2\pi k}{N}(1 - \delta) + 2\phi_k\right] = 0$$

Since the deviations of phases (after fixing all jumps divisible by $\pi$) from a linear behavior are small:

$$\sum_{k=1}^{N} k \cdot a_k^2 \cdot \left[\frac{2\pi k}{N}(1 - \delta) + 2\phi_k\right] = 0 \quad \text{Equation 1}$$

and $$\delta = 1 - \frac{N}{\pi} \frac{\sum_{k=1}^{N} k \cdot a_k^2 \cdot \phi_k}{\sum_{k=1}^{N} k^2 \cdot a_k^2} \quad \text{Equation 2}$$

Equation 2 may be used as an algorithm for overlay measurements for periodic SCOL targets. When target is perfectly symmetric each term in Equation 1 is equal to zero and $\phi_k$ is linear with k, namely, $$\phi_k = \frac{\pi k}{N}(1-\delta).$$

Accordingly, it is natural to define a criterion for target asymmetry as $$\Delta_1 = \frac{N}{\pi} \frac{\sum_{k=1}^{N} k \cdot a_k^2 \cdot \text{abs}\left[\frac{\pi k}{N}(1-\delta) - \phi_k\right]}{\sum_{k=1}^{N} k^2 \cdot a_k^2}$$

Or in more rigorous statistical sense as $$\Delta_2 = \frac{1}{2}\sqrt{\frac{\sum_{k=1}^{N} k^2 \cdot a_k^2 \cdot \left[(1-\delta) - \frac{N}{\pi k}\phi_k\right]^2}{\sum_{k=1}^{N} k^2 \cdot a_k^2}}.$$

FIG. 3B is a schematic illustration exemplifying the quality of the Δ as a criterion for target asymmetry, by a direct comparison to measured AEI (after-etch-inspection)—ADI (after-develop inspection) bias. In FIG. 3B, Δ is taken as $\Delta_2$ according to the expression presented above. The comparison is carried out with respect to the measured sites. For four instances, relating to four specific sites, detailed comparisons 90A-90D of the AEI-ADI biases with the Δ criterion are presented. The target asymmetry criterion may be used to estimate target asymmetry with respect to various wavelengths and to construct various target merits.

In certain embodiments, the methods and systems may be applied to pupil or spectral images as well as to field images. For example, once the pitch of a SCOL target grating is known, one can use a wavelength which is only slightly smaller than the pitch to obtain an image which retains the periodic structure. Measuring, for example by Fourier transform or by Fisher's kappa test, etc., the periodicity of the obtained image yields an indicator of the quality of the target. Such measurement is applicable during the calibration or on the fly to remove or replace defective targets.

The proposed methods of characterizing the target asymmetry in the OVL measurement allow constructing a criterion based on target asymmetry, which provides a quantitative estimation of the effect of such asymmetry. Target asymmetry may be indicated by deviations from linear dependency of the phases of harmonics on harmonic numbers which is characteristic of symmetric signals.

In certain embodiments, target characterization module 140 (e.g., via analysis unit 120) is further arranged to cluster targets 80 according to metrics 110, analyze the clustering to indicate production errors and/or to direct metrology measurements to target clusters to enhance target similarity. The clustering may also be used for enhancing the metrology measurements by directing them at clusters of targets, thus raising the level of target similarity for the measurements (targets in a cluster are more similar to each other than to the whole population of targets). Visualization module 135 may be arranged to visually present target clusters and the statistically derived features of metrics 110 with respect to target positions on wafer 60. Certain embodiments introduce methods of estimating the noise signatures of OVL targets. The compact form of the signatures is further used for an automatic clustering and labeling of different regions of the wafer according to obtained clusters.

By design, the ideal appearance of targets 80 is identical for all sites (i.e. for all dies 70 and die positions) across wafer 60 and invariant to rotation of 180°. Therefore, intra-target differences in appearance on images may be related to the several sources, among those the most influential are: (1) Process variation (defects on the surface of the target), (2) TIS (Tool Induced Shift); (3) Optics-related noise (such as camera noise or cross-talk). The task of analyzing and estimating the effect of each type of noise from single target image is very challenging. Distinguishing characteristic patterns may be carried out by analyzing target behavior in sub samples of targets 80 to provide insights on the sources of noise behavior on wafer 60.

The proposed approach may comprise the following steps: (1) Acquisition: Sampling 2D images of target 80 (e.g., overlay targets) on wafer 60 using both 0° and 180° rotations (the acquisition may be performed during a training stage and thus not require extra stage movements). (2) Registration: Building an initial reference target using accurate registration (with sub-pixel accuracy) of the acquired target images and taking into account local symmetries of each target (by design). (3) Noise estimation: Estimating the additive noise per site (and rotation angle) using the reference target as a model. (4) Compression: Each 2D noise map image may be converted into a compact vector signature using dimensionality reduction techniques. (5) Clustering: Unsupervised machine learning techniques may be used to cluster the noise signatures according to their appearance. (6) Analysis: The effects of additive noise may be analyzed with respect to the expected similar behavior for measurements made on targets from the same cluster. In addition, the symmetry properties of the noise signature may be used to understand and discriminate the sources of the noise using rules such as, for example: if the noise signature "rotates" with the acquisition angle, it may be related to the process; if the noise signature does not "rotate" with the acquisition angle it may be related to TIS. (7) Visualization of clusters on the wafer may provide a clue for deciding on exclusion zones. By combining additional quantitative characteristics proposed in the present disclosure, the noise signatures may be related with specific kernel characteristics as expressed by appropriate metrics 110 (e.g., the symmetry and the periodicity quality measurements).

FIGS. 4A, 4B are high level schematic illustrations of target clustering and cluster visualization, according to some embodiments of the invention. FIG. 4A schematically illustrates a first part 132A of a visualization of the clustered targets, namely the visualization of representatives from each cluster of noise signatures. The non-limiting example presents box in box targets exhibiting three noise signature clusters 83A (symmetric noise signature) and 83B, 83C (reciprocally asymmetric noise signatures). FIG. 4B schematically illustrates a second part 132B of a visualization of the clustered targets, namely a schematic illustration which associates for each target (illustration 86), the distribution of the types of noise signatures (83A, indicated as "2", 83B, indicated as "1", and 83C, indicated as "3") among dies 70. Each distribution unit 84 is denoted by a pair of numbers that designates the types of noise signature under target acquisition for no rotation (left number in each pair) and 180° rotation (right number in each pair). In the illustrated example, noise signature types 83B, indicated as "1", and 83C, indicated as "3" are symmetric, providing evidence for TIS-related variability. Additionally, visualization 132B suggests the noise signature in the center of wafer (central nine units 84A corresponding to central nine dies 70) is much more stable than in the periphery (peripheral 18 units 84B corresponding to peripheral 18 dies 70).

In certain embodiments, metrology system 100 further comprises a scatterometry overlay (SCOL) measurement subsystem 150 (FIG. 1B) arranged to carry out SCOL measurements on the targets, where the SCOL measurement subsystem 150 includes a target weighting module 155, and a user interface 160 arranged to allow a user to influence target weights relating to the SCOL measurements. Target characterization module 140 may be further arranged to analyze targets 80 (e.g., the target images or signals received from the targets, see, e.g., FIGS. 2I and 2J) using the analyzed metric(s) and with respect to the SCOL measurements and to enhance the SCOL measurements by weighting targets 80 with respect to the characterization of targets 80. Target imaging and analysis may be used to enhance SCOL measurements and improve their accuracy and be carried out prior to the actual SCOL measurements (e.g., in a training stage) or in real time during the SCOL measurements. In the context of SCOL, target weightings and the metrics may be selected to identify sources for total measurement uncertainty (TMU) and for correctable error sources and to minimize the error introduced by residual correctable error sources and be residual error sources. In certain embodiments, system 100 may be used for removing outliers (extremely divergent targets, thereby reducing residual errors predictably and using quantitative criteria.

Certain embodiments comprise visual user interface 160 for metrology system 100. Visual user interface 160, which is at least partially implemented in computer hardware, may be arranged to visually present at least one metric with respect to target positions on wafer 60, wherein the at least one metric is calculated from a plurality of measured target signals (e.g., kernels 90 from specified ROIs 85) from corresponding targets 80 on wafer 60, using respective functions. Visual user interface 160 may be further arranged to allow a user to influence target weights relating to SCOL measurements by the metrology system. In certain embodiments, user interface 160 may comprise any of visualization module 135, visualizations 130 of characterized targets and visualizations 132 of clustered targets.

Figure 5:
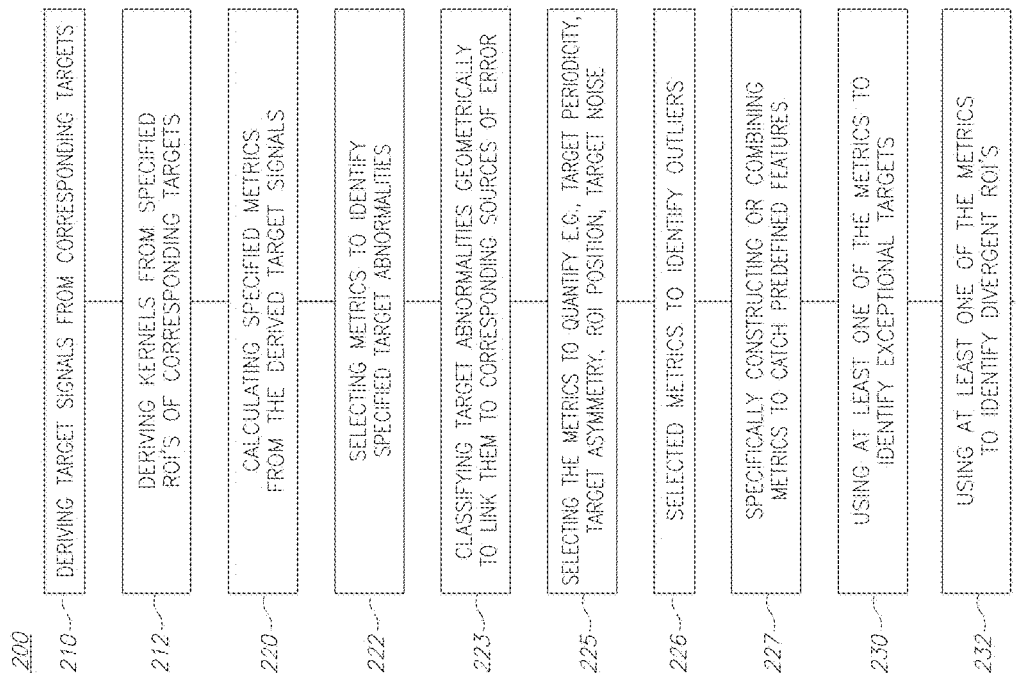
FIG. 5 is a high level schematic flowchart of a method according to some embodiments of the invention.

FIG. 5 is a high level schematic flowchart of a method 200 according to some embodiments of the invention. Method 200 may comprise deriving a plurality of target signals (e.g. kernels from specified regions of interest (ROIs) 212) from corresponding targets on a wafer (stage 210); calculating at least one specified metric from the derived target signals using respective functions (stage 220); and analyzing the at least one metric to characterize the targets (stage 240). Deriving 210, calculating 220 and/or analyzing 240, as well as any of the following stage may be carried out by at least one computer processor.

Generally, method 200 may be carried out to identify errors in the production of the targets and/or the wafer, to characterize identified errors with respect to the metrics and to recover a metrology measurement process and/or a production process if possible, as well as assess recoverability thereof. Method 200 may comprise selecting metrics to identify specified target abnormalities (stage 222) and classifying target abnormalities geometrically to link them to corresponding sources of error (stage 223).

In certain embodiments, multiple target signals may be derived from different parts of one target, such as target elements on different layers, inner and outer target elements, etc. The analysis may compare target signals from different parts of the targets, and appropriate metrics may be applied to identify abnormalities within targets. In certain embodiments, method 200 may be carried out with respect to a plurality of specified metrics and analyzing 240 may be carried out statistically with respect to the metrics. The metrics may be selected (stage 225) to quantify target regularity, target asymmetry and/or ROI position in the target; metrics may be selected to identify (and eventually remove) outliers (stage 226), and the metrics may be used to identify exceptional targets (stage 230) or divergent ROIs (stage 232) as non-limiting examples. Method 200 may further comprise using the metrics to compare target signals with respect to different target position in the die and/or with respect to different die position on the wafer (stage 234). Method 200 may further comprise specifically constructing or combining metrics to catch predefined features (stage 227).

In certain embodiments, method 200 may further comprise visualizing the at least one metric with respect to target positions on the wafer (stage 260) and visualizing statistically derived features of the metrics with respect to target positions on the wafer (stage 262). In certain embodiments, method 200 may further comprise clustering targets according to the metrics (stage 250) and analyzing the clustering to indicate production errors (stage 252) and/or directing metrology measurements to target clusters to enhance target similarity (stage 254). Respectively, method 200 may further comprise visualizing the target clusters (stage 265). Clustering the targets 250 may be preceded by target image acquisition, registration of the acquired images to provide a reference target (stage 247), estimation of the additive noise using the reference target as a model (stage 248) and compression of each noise map into a compact vector signature (stage 249), as described above.

In certain embodiments, method 200 may be carried out during scatterometry overlay (SCOL) measurements and further comprise analyzing the targets using the at least one analyzed metric and with respect to the SCOL measurements (stage 270), e.g. target analysis may relate to target images, target asymmetry measures, ROI parameters, target clustering or any other criterion which is derived from any of the applied metrics. Method 200 may further comprise enhancing the SCOL measurements by weighting the targets with respect to the target analysis (stage 280) and providing a user interface that allows the user to influence the target weights (stage 282), e.g. in order to optimize SCOL measurements by the metrology system. In embodiments, a statistical analysis of a plurality of metrics may be carried out to analyze the targets and to indicate targets which optimize SCOL accuracy (284). In certain embodiments, method 200 may comprise weighting a plurality of metrics according to the extent the respective target abnormalities (which the respective metrics is selected to identify, stage 222) influence the corresponding metrology measurements (stage 275).

In certain embodiments, method 200 may further comprise using metrics to optimize the wavelength selection for the metrology measurements (stage 305), running a wavelength calibration (stage 310), comparing the calibration target signals per wavelength to previous values and with measurement specifications (stage 312) and reiterating the calibration and comparison until a criterion (e.g. a threshold for an allowed deviation, variation among the targets or among wavelengths) relating the comparison results and the specifications is met (stage 314).

In certain embodiments, method 200 may further comprise a training stage (stage 320) in which optimization parameters (e.g., wavelength, focus, ROI) are selected (stage 322) and then measured and analyzed with respect to characterization metrics (stage 324). For example, method 200 may comprise increasing signal accuracy by judiciously selecting ROI's to include correct target parts (stage 325), possibly under consideration of different target layers. The training stage may thus result in system adjustment and setup robustness verification (stage 326). During runs, method 200 may also comprise checking the targets with respect to their asymmetry, or any other characteristic, and if needed applying a recovery procedure (optionally including clustering) or dismissing the measurement.

Certain embodiments provide mathematical characterization of target signals such as kernels, spectra and/or pupil images for different optimizations, recipe building, flier detection and defected target recognition. Certain embodiments measure the asymmetry of target signals such as kernel, spectra, and/or pupil images for different optimizations or recipe building, including flier detection. Certain embodiments comprise simultaneous use of these aspects to further enhance recipe building and flier detection. Certain embodiments provide an imaging tool inspection on scatterometry targets.

Certain embodiments may be implemented in the form of a software package to be integrated in the overlay metrology tools. The characterization and classification of the OVL measurement may be used for automatic and semi-automatic calibration and optimization of the metrology tools during training and running stages for the improvement of measurement accuracy (e.g., with respect to wavelength, focus, ROI, etc.). Certain embodiments may also contribute to data analysis in case of unexpected performance degradation.

In certain embodiments, the target selection, characterization, flier detection and/or recipe optimization may be based on considering either OVL measurement calculation of the physical raw signal or some integral of the raw signal and not on the resulting overlay. The raw measurement output could be the target signal such as kernels, spectra or pupil image. Target selection may refer to physical raw signal patterns observed on the wafer which may be caused by the process or by the measurement.

Advantageously, the disclosed methods and system do not rely on an exact physical understanding of the sources of errors (as do regression methods and methods based on electromagnetic analysis), do not depend on known target parameters (which limits the use and repeatability of methods based on target parameters) and relate directly to overlay inaccuracies (and not indirectly to algorithmic aspects or to separate testing processes).

In certain embodiments, assuming the low dependence of the raw signal on process variation of under-layers (not on the process or resist layers), the similar processing of process and resist layers must result in targets with measured signals that are close one to another. Thus, in case fluctuations of the signal characteristics other than pure OVL are observed, these may indicate that some change occurred during the production process of the measured layers.

Advantageously, combinations of the above described approaches may enhance and improve the accuracy of OVL measurement results as well as the OVL modeling. In certain embodiments, each layer measurement signal may be analyzed in a number of ways depending on the targets' specifications. For example: a) a separation approach, which analyses the targets' measurement signal separately per layer, axis, measurement rotation, etc. b) a non-separation approach, in which for each layer the averaging process takes place by separation characteristics such as wavelength, focus, ROI, etc. The measurement signals are compared to each other by quantitative characteristics, for example: spectral analysis-derived features or statistical tests such as Fisher's Kappa and Kolmogorov-Smirnov statistics which provide raw signal characterization, cross correlation with some arbitrary chosen signal, etc. In certain embodiments, the deviation of phase behavior with frequency from linear behavior is calculated and transforms this deviation to an error range in nanometers. In certain embodiments, the mapping of the noise signature on the wafer involves methods from image analysis for noise estimation. Then, the unsupervised machine learning technique for clustering of the OVL targets is applied according to their corresponding noise signature.

Additionally, the target characterization may be used to detect fliers and clusters in field (die) and wafer levels to allow the user to select a preferred treatment, for example: a) for damaged targets due to various causes such as measurement set-up problems, target quality problems, etc., the user may choose to eliminate the respective targets from the measurements metric calculation in order to improve accuracy, b) for targets which differ from each other, the user may choose a set of similar targets to achieve stability and accuracy of the measurement (or such solution may be fully automatic), c) the system may be configured to detect the best compatible recipe set-up in terms of wavelength, focus, ROI, etc. by its quality, stability, consistency, and by its white noise.

Advantageously, the disclosed methods detect fliers and clusters at zone and test (target) levels, which are caused by systematic or random effects. The methods and systems provide an understanding of the major contributions to inaccuracy and instability for the conventional metrics and assist the user to optimize the setups to increase the accuracy and reliability. In particular, certain embodiments improve the accuracy of the OVL process control, to fit to the tightening node requirements.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A method comprising:
   acquiring, with an overlay metrology tool, a plurality of overlay metrology target signals from a set of targets on a wafer, wherein at least some of the plurality of overlay metrology target signals are acquired from different target elements of a single target of the set of targets;
   executing a target characterization module with a processor;
   calculating, with the target characterization module, a plurality of metrics for each of the acquired plurality of target signals;
   analyzing, with the target characterization module, the calculated plurality of metrics to determine one or more features of at least one target of the set of targets;
   clustering, with the target characterization module, two or more targets of the set of targets according to the calculated plurality of metrics;
   analyzing the clustered two or more targets of the set of targets to identify one or more production errors on the wafer; and
   configuring the overlay metrology tool based on the identified one or more production errors to improve measurement accuracy during one or more metrology processes.

2. The method of claim 1, further comprising visualizing the calculated plurality of metrics with respect to a position of the at least one target of the set of targets on the wafer.

3. The method of claim 1, wherein the analyzing comprises a statistical analysis of the calculated plurality of metrics.

4. The method of claim 1, further comprising using at least one of the calculated plurality of metrics to identify outlier targets.

5. The method of claim 1, further comprising visualizing the clustering of the two or more targets.

6. The method of claim 1, further comprising clustering one or more targets according to the calculated plurality of metrics, and directing the overlay metrology tool to measure one or more target clusters.

7. The method of claim 1, further comprising visualizing one or more determined features of the calculated plurality of metrics with respect to a position of the at least one target of the set of targets on the wafer.

8. The method of claim 1, further comprising selecting the calculated plurality of metrics to quantify, with respect to one or more targets of the set of targets, at least one of: periodicity, symmetry, declination, self-correlation, statistically derived features, and parameters of one or more Fourier transformed target signals.

9. The method of claim 1, wherein the one or more overlay metrology target signals are one or more kernels from one or more specified regions of interest (ROIs) of the corresponding targets.

10. The method of claim 9, further comprising selecting the calculated plurality of metrics to quantify an ROI position in one or more targets of the set of targets or to identify one or more outlier ROIs in the one or more targets.

11. The method of claim 1, wherein the one or more overlay metrology target signals are acquired during one or more scatterometry overlay (SCOL) measurements, the method further comprising analyzing one or more target images using the calculated plurality of metrics and the one or more SCOL measurements.

12. The method of claim 11, further comprising weighting the one or more targets of the set of targets.

13. The method of claim 12, wherein the analyzing is carried out statistically with respect to the calculated plurality of metrics, the method further comprising using the calculated plurality of metrics to identify one or more targets to optimize SCOL accuracy.

14. The method of claim 1, wherein the one or more metrology processes includes calibration of the overlay metrology tool.

15. The method of claim 1, wherein the one or more metrology processes includes operation of the overlay metrology tool during at least one of a training stage or a running stage.

16. A metrology system comprising:
   an overlay metrology tool, wherein the overlay metrology tool acquires a plurality of overlay metrology target signals from a set of targets on a wafer, wherein the overlay metrology tool acquires at least some of the plurality of overlay metrology target signals from different target elements of a single target of the set of targets; and
   a processor, wherein the processor is configured to execute a target characterization module, wherein the target characterization module is configured for:
      calculating a plurality of metrics for the acquired plurality of overlay metrology target signals;
      analyzing the calculated plurality of metrics to determine one or more features of at least one target of the set of targets;
      clustering two or more targets of the set of targets according to the calculated plurality of metrics;
      analyzing the clustered two or more targets of the set of targets to identify one or more production errors on the wafer; and
      configuring the overlay metrology tool based on the identified one or more production errors to improve measurement accuracy during one or more metrology processes.

17. The metrology system of claim 16, wherein the processor is configured to execute a target visualization module configured for visually presenting the calculated plurality of metrics with respect to one or more target positions on the wafer.

18. The metrology system of claim 16, wherein the target characterization module is configured for characterizing one or more targets by a statistical analysis of the calculated plurality of metrics, wherein the calculated plurality of metrics are selected to quantify, with respect to one or more targets of the sets of targets, at least one of periodicity, symmetry, declination, self-correlation, statistically derived features, or one or more parameters of one or more Fourier transformed target signals.

19. The metrology system of claim 16, wherein the one or more overlay metrology target signals are one or more kernels from specified regions of interest (ROIs) of the corresponding targets.

20. The metrology system of claim 19, wherein the target characterization module is further configured for quantifying an ROI position in one or more targets or to identify divergent ROIs in the one or more targets.

21. The metrology system of claim 16, wherein the processor is configured to execute a visualization module configured for visually presenting at least one target cluster and one or more determined features of the calculated plurality of metrics with respect to a position of one or more targets of the set of targets on the wafer.

22. The metrology system of claim 16, wherein the target characterization module is further configured for clustering one or more targets according to the calculated plurality of metrics, wherein the processor is further configured to direct the optical metrology tool to measure one or more target clusters.

23. The metrology system of claim 16, further comprising a scatterometry overlay (SCOL) measurement subsystem configured for carrying out one or more SCOL measurements on the set of targets, wherein the target characterization module is further configured for analyzing the set of targets using the calculated plurality of metrics and the one or more SCOL measurements, and enhancing the SCOL measurements by weighting one or more targets of the set of targets.

24. The metrology system of claim 23, further comprising a user interface configured for allowing a user to influence one or more target weights associated with the one or more SCOL measurements.

* * * * *